United States Patent [19]

Moriuchi et al.

[11] Patent Number: 4,699,617
[45] Date of Patent: Oct. 13, 1987

[54] FLOWMETER

[75] Inventors: Yousuke Moriuchi; Tadashi Kousai, both of Fujinomiya, Japan

[73] Assignee: Terumo Corporation, Tokyo, Japan

[21] Appl. No.: 925,254

[22] Filed: Oct. 31, 1986

[30] Foreign Application Priority Data

Oct. 31, 1985 [JP] Japan ................ 60-244364

[51] Int. Cl.4 .................. A61M 5/00; G01P 5/00
[52] U.S. Cl. ......................... 604/246; 73/861.57
[58] Field of Search ............... 604/127, 246, 254; 73/861.55, 861.57

[56] References Cited

U.S. PATENT DOCUMENTS

| 2,778,223 | 1/1957 | Kimbrell | 73/861.55 |
| 3,034,504 | 5/1962 | Winsor | 73/861.55 |
| 3,049,918 | 8/1962 | Sparkuhl | 604/246 X |
| 3,587,313 | 6/1971 | Smith | 73/861.57 |

FOREIGN PATENT DOCUMENTS 1923589 5/1969 Fed. Rep. of Germany .
50-31466 10/1975 Japan .

Primary Examiner—Dalton L. Truluck
Attorney, Agent, or Firm—Cushman, Darby & Cushman

[57] ABSTRACT

A flowmeter has a main body having fluid inlet and outlet passages and a vertical fluid channel formed in the main body and having one end communicating with the inlet passage and the other end communicating with the outlet passage. The vertical fluid channel has a first passage and a second passage having a cross-sectional area larger than that of the first passage. The first passage has therein a float for regulating a flow rate of the fluid flowing therethrough, and is tapered to have a cross-sectional area increasing from the inlet passage side toward the outlet passage side such that the float remains in position when the fluid passes through the first passage. The second passage has therein a valve for opening the second passage when the fluid is to flow therethrough and for closing the second passage when the fluid is not to flow therethrough. The valve has a projection for moving the float toward the inlet passage when the second passage is closed. The float and the valve have specific gravities larger or smaller than that of the fluid.

7 Claims, 7 Drawing Figures

FIG. 6
FIG. 7
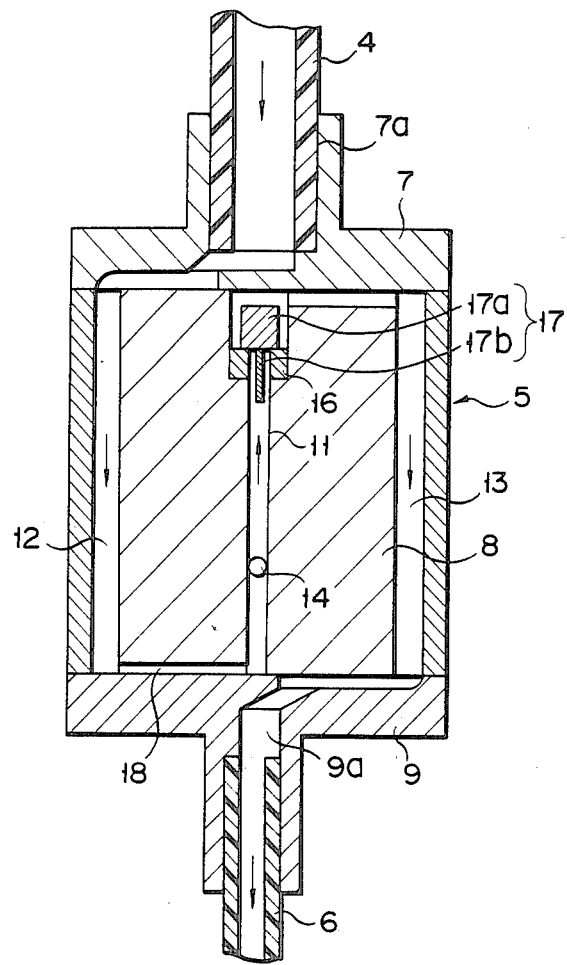
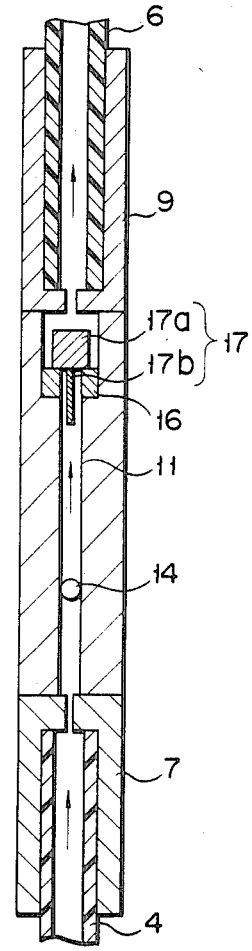

FLOWMETER

BACKGROUND OF THE INVENTION

1. Field of the Invention

The present invention relates to a flowmeter and, more particularly, to a flowmeter to be assembled in a fluid therapy line for continuously injecting a therapeutic fluid into the body of a patient at a very low rate in order to prevent formation of a thrombus in a catheter when the catheter is indwelled in the patient's body over a relatively long period of time in an invasive blood pressure monitoring system or the like.

2. Description of the Prior Art

Conventionally, a fluid therapy line has an intravenous drip chamber for measuring the flow rate of a therapeutic fluid injected into a patient's body. Such an intravenous drip chamber is also used in an invasive blood pressure monitoring system. However, flow rate measurement with an intravenous drip chamber requires a relatively long period of time and may cause introduction of air into the patient's body during flushing or the like.

As a fluid therapy flowmeter free from this problem, a flowmeter using a float is described in U.S. Pat. No. 3,034,504 or Japanese Patent Publication No. 50-31466. However, when this type of flowmeter is assembled in an invasive blood pressure monitoring system connected to a flushing device, the float is caused to abut against the wall of the fluid outlet port by the excess fluid flowing during flushing. Even after the flow rate recovers to the normal value, the float remains attached to the wall and does not return to the original position. Then, a prescribed micro flow rate cannot be obtained, resulting in an unsatisfactory result.

SUMMARY OF THE INVENTION

It is, therefore, an object of the present invention to provide a flowmeter wherein even if the float abuts against and becomes attached to the wall of the fluid outlet port due to flow of excess fluid flowing during flushing, the float can be allowed to fall to the original position and the flow rate can be recovered to the original value.

According to the present invention, there is provided a flowmeter comprising:

a main body having fluid inlet and outlet passages; and a vertical fluid channel formed in the main body and having one end communicating with the inlet passage and the other end communicating with the outlet passage, the vertical fluid channel having a first passage and a second passage having a cross-sectional area larger than that of the first passage, the first passage having therein a float for regulating a flow rate of the fluid flowing therethrough, the first passage being tapered to have a cross-sectional area thereof increasing from the inlet passage side toward the outlet passage side such that the float remains in position when the fluid passes through the first passage, the second passage having therein valve means for opening the second passage when the fluid is to flow therethrough and for closing the second passage when the fluid is not to flow therethrough, the valve means having a projection for moving the float toward the inlet passage when the second passage is closed, and the float and the valve means having specific gravities larger than that of the fluid when the first passage is arranged below the second passage, and having specific gravities smaller than that of the fluid when the first passage is arranged above the second passage.

BRIEF DESCRIPTION OF THE DRAWINGS

FIGS. 6 and 7 are longitudinal sectional views showing third and fourth embodiments of the present invention wherein tapered shapes are different.

DETAILED DESCRIPTION OF THE PREFERRED EMBODIMENTS

The present invention will be described in detail hereinafter.

Figure 1:
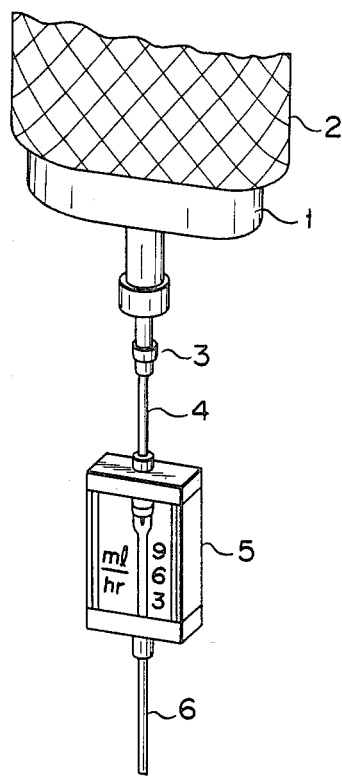
FIG. 1 is a perspective view showing a flowmeter according to the present invention when it is assembled in a fluid therapy line.

FIG. 1 shows a flowmeter according to the present invention, which is connected to a fluid therapy line. Fluid therapy bag 1 is compressed at a pressure of, e.g., 300 mmHg in pressure bag 2. Flowmeter 5 of the present invention is connected to bag 1 through cannula 3 and connecting tube 4. The outlet port of flowmeter 5 is connected to a flushing device (not shown) through fluid therapy tube 6. Therapeutic fluid is injected into the patient's body through this line system and an indwelling catheter.

Figure 2:
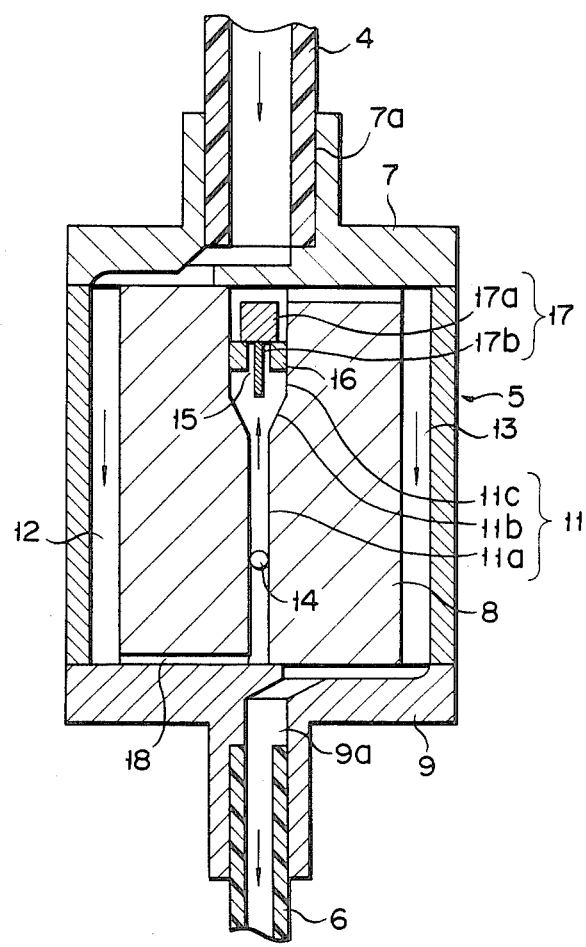
FIG. 2 is a longitudinal sectional view showing a flowmeter according to a first embodiment of the present invention.

FIG. 2 shows the section of flowmeter 5 according to the first embodiment of the present invention. Flowmeter 5 consists of upper cap 7, main body 8, and lower cap 9. These three members are usually plastic molded members and is preferably formed of, e.g., a transparent resin such as polystyrene, polymethyl methacrylate, polycarbonate or the like. The three molded members are adhered by adhesion with a solvent, adhesion with an adhesive, or ultrasonic welding.

Upper cap 7 has fluid inlet passage 7a which receives connecting tube 4. Lower cap 9 has fluid outlet passage 9a which receives fluid therapy tube 6.

Vertical channel 11 is formed at the center of main body 8. Channel 11 has small-diameter portion 11a, tapered portion 11b, and large-diameter portion 11c. Portion 11a is tapered such that a lower ⅔ portion of channel 11 has an inner diameter slightly smaller than that of the remaining upper portion. Portions 11b and 11c are continuous with portion 11a.

Float 14 for regulating the flow rate of the fluid is arranged in small-diameter portion 11a of vertical channel 11. Float 14 preferably has a spherical shape and has a specific gravity larger than that of the fluid. Float 14 is set such that the flow rate is defined by the difference in diameter of float 14 and portion 11a. Examples of the material for float 14 include glass, ruby, stainless steel, plastic, or carbon. These materials have different specific gravities. In order to allow the float to be stably positioned at a prescribed position at a predetermined flow rate, the diameter of portion 11a must be selected in accordance with the specific gravity of the material selected for float 14. For example, if the therapeutic fluid is flowed at a very small, constant rate of 2 to 4 ml/hour as in a continuous micro rate fluid therapy line connected to a flushing device, carbon or plastic having a small specific gravity is preferable since it allows a larger diameter difference with respect to portion 11a. In this case, spherical float 14 preferably has a diameter of 0.8 mm and small-diameter portion 11a preferably has a diameter of 0.9 to 1.0 mm. If the therapeutic liquid flows at a normal rate of 2 to 4 ml/hour, the scale is set at a predetermined position on the outer surface of portion 11a, as shown in FIG. 1. When the flow rate is, e.g., 3 ml/hour, the tapered diameter of portion 11a is set such that the float stops at a position corresponding to the scale value of 3 ml/hour.

Large-diameter portion 11c of vertical channel 11 has a diameter three times or more of that of small-diameter portion 11a. Closure member 16 crosses portion 11c and has narrow communication portion 15 at its central portion. Valve 17 is arranged in closure member 16. Valve 17 consists of head 17a arranged on closure member 16 and rod 17b connected to head 17a. Rod 17b is inserted in communication portion 15 of closure member 16 with a gap. Valve 17 preferably has a large specific gravity and high corrosion resistance and preferably consists of stainless steel. As will be described later, due to the flow of excess therapeutic fluid during flushing, valve 17 abuts against the inner wall of upper cap 7. In this case, however, rod 17b is preferably located at least inside communication portion 15. In particular, the lower portion of valve 17 is preferably located at the same level or lower than the upper half of closure member 16. The gap between communication portion 15 and rod 17b inserted therein must be smaller than the diameter of float 14 so as not to allow float 14 to pass therethrough.

First and second side channels 12 and 13 are formed at the side portion of main body 8. First side channel 12 allows the fluid to flow from inlet passage 7a to the bottom of channel 11. Second side channel 13 allows the fluid to flow from the top of vertical channel 11 to outlet passage 9a. In order to allow float 14 to stay in channel 11, the level of cross passage 18 connecting channels 11 and 12 must have a diameter smaller than that of float 14.

Figure 5:
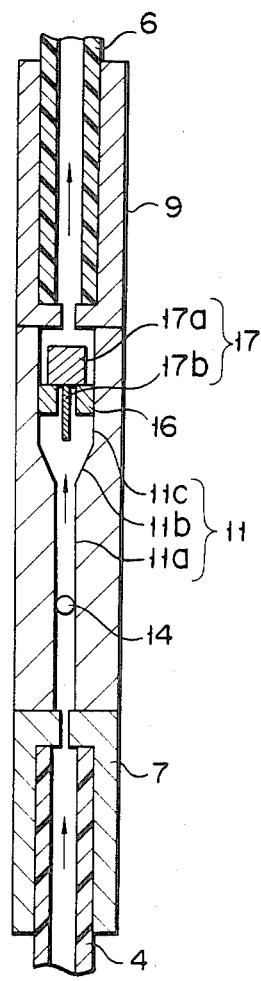
FIG. 5 is a longitudinal sectional view showing a second embodiment of the present invention.

FIG. 5 shows a longitudinal sectional view of a flowmeter according to a second embodiment of the present invention. In the flowmeter shown in FIG. 5, the inlet and outlet passages are simplified. More specifically, the inlet passage defined by tube 4 is connected to the bottom of channel 11, and the outlet passage defined by tube 6 is connected to the top of channel 11. This flowmeter operates in the same manner as that of the first embodiment.

FIGS. 6 and 7 show flowmeters according to the third and fourth embodiments of the present invention. FIG. 6 shows a longitudinal sectional view of a flowmeter having the same configuration as that shown in FIG. 2 except that tapered portion 11b is omitted. FIG. 7 shows a longitudinal sectional view of a flowmeter having the same configuration as that shown in FIG. 5 except that tapered portion 11b is omitted. The flowmeters shown in FIGS. 6 and 7 operate in the same manner as that of the first embodiment.

When a therapeutic fluid is flowed at a normal rate of 2 to 4 ml/hour, valve 17 is located at the position shown in FIG. 2. The fluid flowing in through inlet passage 7a flows down in channel 12 and reaches vertical channel 11. The fluid then flows up channel 11 and flows out through outlet passage 9a via channel 13. Since the therapeutic fluid is compressed at a predetermined pressure as described above, valve 17 slightly floats to assure the small rate flow passage of the fluid. If required, the upper surface of closure member 16 can be slightly inclined. In this case, the flow passage is more easily obtained.

Figure 3:
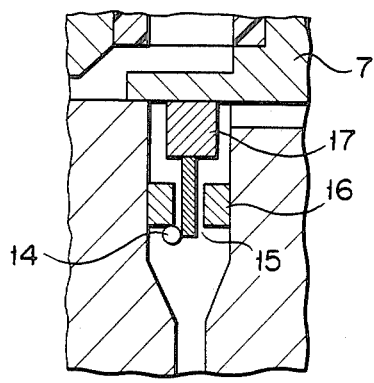
FIGS. 3 and 4 are sectional views for explaining the operation of the flowmeter according to the present invention.

During priming or flushing for blood cleaning in a fluid therapy line including a flowmeter as described above, the therapeutic fluid flows at a flow rate of 2,400 to 7,200 ml/hour. This flow rate is 1,000 times or more that in constant, micro rate fluid therapy. When the flow rate during flushing is set at 3,000 ml/hour and the diameter of portion 11a of vertical channel 11 is set at 1 mm, the linear velocity of the fluid in portion 11a is about 100 cm/sec. Float 14 then abuts against the upper wall (i.e., closure member 16) at this velocity. With this impact, float 14 tightly adheres to closure member 16 and will not be allowed to fall even after the flow rate recovers to the normal value (FIG. 3). In this state, the flow rate of therapeutic fluid cannot be measured.

Figure 4:
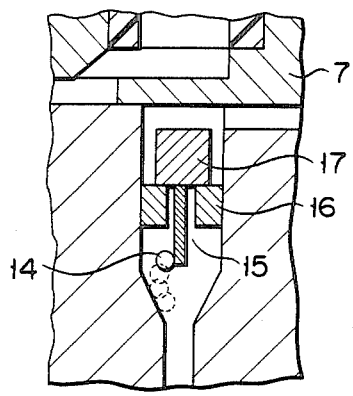

If valve 17 is included according to the present invention, it is also moved upward upon flow of excess fluid as shown in FIG. 3. However, when the flow rate recovers to the normal value, valve 17 falls by its own weight. Then, rod 17b contacts float 14 to strike it down to its original position, thereby allowing flow rate measurement (FIG. 4).

In summary, according to the present invention, even if flushing is performed with an excessive amount of a therapeutic fluid, when the flow rate recovers to the normal value, the float is allowed to fall to its original position by valve 17. Normal flow rate measurement can then be initiated immediately.

What is claimed is:

1. A flowmeter comprising:
   a main body having fluid inlet and outlet passages; and
   a vertical fluid channel formed in said main body and having one end communicating with said inlet passage and the other end communicating with said outlet passage,
   said vertical fluid channel having a first passage and a second passage having a cross-sectional area larger than that of said first passage,
   said first passage having therein a float for regulating a flow rate of the fluid flowing therethrough,
   said first passage being tapered to have a cross-sectional area thereof increasing from said inlet passage side toward said outlet passage side such that said float remains in position when said fluid passes through said first passage,
   said second passage having therein valve means for opening said second passage when the fluid is to flow therethrough and for closing said second passage when the fluid is not to flow therethrough,
   said valve means having a projection for moving said float toward said inlet passage when said second passage is closed, and
   said float and said valve means having specific gravities larger than that of said fluid when said first passage is arranged below said second passage, and having specific gravities smaller than that of said fluid when said first passage is arranged above said second passage, and having specific gravities smaller than that of said fluid when said first passage is arranged above said second passage.

2. A flowmeter according to claim 1, further comprising a closure member arranged in said second passage and having a narrow communication portion for receiving said projection, and wherein said valve means has a head with said projection, said head being supported by said closure member.

3. A flowmeter according to claim 1, wherein said second passage consists of a large-diameter portion having a cross-sectional area larger than that of said first passage, and a tapered portion connecting said large-diameter portion and said first passage.

4. A flowmeter according to claim 1, wherein said inlet passage communicates with the bottom of said vertical channel through a first side channel, and said outlet passage communicates with the top of said vertical channel through a second side channel.

5. A flowmeter according to claim 1, wherein said inlet passage, said vertical channel, and said outlet passage are aligned on a substantially straight line.

6. A flowmeter according to claim 1, wherein said first and second passages are connected.

7. A flowmeter according to claim 1, wherein said float is spherical.

* * * * *